United States Patent
Brucker et al.

(10) Patent No.: US 10,248,796 B2
(45) Date of Patent: Apr. 2, 2019

(54) ENSURING COMPLIANCE REGULATIONS IN SYSTEMS WITH DYNAMIC ACCESS CONTROL

(71) Applicants: Achim D. Brucker, Karlsruhe (DE); Helmut Petritsch, Karlsruhe (DE)

(72) Inventors: Achim D. Brucker, Karlsruhe (DE); Helmut Petritsch, Karlsruhe (DE)

(73) Assignee: SAP SE, Walldorf (DE)

(*) Notice: Subject to any disclaimer, the term of this patent is extended or adjusted under 35 U.S.C. 154(b) by 515 days.

(21) Appl. No.: 14/325,551

(22) Filed: Jul. 8, 2014

(65) Prior Publication Data

US 2016/0012242 A1 Jan. 14, 2016

(51) Int. Cl.
| | |
|---|---|
| *G06F 21/60* | (2013.01) |
| *G06F 21/62* | (2013.01) |
| *G06F 21/41* | (2013.01) |
| *G16H 10/60* | (2018.01) |

(52) U.S. Cl.
CPC ............ *G06F 21/604* (2013.01); *G06F 21/41* (2013.01); *G06F 21/62* (2013.01); *G06F 21/6245* (2013.01); *G16H 10/60* (2018.01)

(58) Field of Classification Search
CPC .... G06F 21/6245; G06F 21/41; G06F 19/322; G06F 21/604; G06F 21/62; G16H 10/60
See application file for complete search history.

(56) References Cited

U.S. PATENT DOCUMENTS

| | | | |
|---|---|---|---|
| 6,412,070 B1 * | 6/2002 | Van Dyke | G06F 9/468 707/999.009 |
| 6,854,014 B1 | 2/2005 | Amin | |
| 7,350,226 B2 * | 3/2008 | Moriconi | G02B 6/132 257/E21.251 |
| 7,363,650 B2 * | 4/2008 | Moriconi | G02B 6/132 257/E21.251 |
| 7,734,682 B2 | 6/2010 | Aubry | |
| 8,056,802 B2 | 11/2011 | Gressel | |
| 8,200,527 B1 | 6/2012 | Thompson | |
| 8,316,051 B1 * | 11/2012 | Burns | G06F 21/6227 707/694 |
| 8,473,505 B2 | 6/2013 | Brucker et al. | |
| 2002/0152319 A1 | 10/2002 | Amin | |
| 2003/0023880 A1 | 1/2003 | Edwards | |
| 2003/0131073 A1 | 7/2003 | Lucovsky | |
| 2003/0159070 A1 | 8/2003 | Mayer | |

(Continued)

OTHER PUBLICATIONS

U.S. Appl. No. 13/925,051, filed Jun. 24, 2013, Brucker et al.
U.S. Appl. No. 13/932,357, filed Jul. 1, 2013, Brucker et al.
U.S. Appl. No. 13/932,388, filed Jul. 1, 2013, Brucker et al.

*Primary Examiner* — Tamara T Kyle
(74) *Attorney, Agent, or Firm* — Fish & Richardson P.C.

(57) ABSTRACT

Methods, systems, and computer-readable storage media for enforcing dynamic access control constraints of a plurality of access control policies, and actions include receiving a set of ordered policies, determining a set of active policies including one or more policies in the set of ordered policies, determining an access control decision based on at least a first policy in the set of active policies, the access control decision being based on determining whether one of a permit decision and a deny decision is inherited from a second policy in the set of ordered policies, and transmitting the access control decision for enforcement of the access control policy.

20 Claims, 4 Drawing Sheets

(56) References Cited

U.S. PATENT DOCUMENTS

| | | |
|---|---|---|
| 2004/0010709 A1 | 1/2004 | Baudoin |
| 2004/0267552 A1 | 12/2004 | Gilliam |
| 2005/0182958 A1 | 8/2005 | Pham |
| 2005/0198247 A1 | 9/2005 | Perry |
| 2008/0022362 A1 | 1/2008 | Hinton |
| 2008/0098453 A1 | 4/2008 | Hinton |
| 2008/0270802 A1 | 10/2008 | Ashley |
| 2009/0077105 A1 | 3/2009 | DeAnna |
| 2009/0178102 A1* | 7/2009 | Alghathbar ......... G06F 21/6218 726/1 |
| 2009/0320093 A1 | 12/2009 | Glazier et al. |
| 2010/0251329 A1 | 9/2010 | Wei |
| 2010/0332504 A1 | 12/2010 | Brucker et al. |
| 2011/0314261 A1 | 12/2011 | Brucker et al. |
| 2012/0137309 A1 | 5/2012 | Makam |
| 2012/0284767 A1 | 11/2012 | Hockings |
| 2013/0019002 A1* | 1/2013 | Heileman ................ G06F 21/10 709/223 |
| 2014/0068697 A1 | 3/2014 | Brucker et al. |

* cited by examiner

ENSURING COMPLIANCE REGULATIONS IN SYSTEMS WITH DYNAMIC ACCESS CONTROL

BACKGROUND

Modern enterprise systems, e.g., enterprise resource planning (ERP) systems, customer relationship management (CRM) systems, enforce a variety of different and complex security policies. Moreover, more and more enterprises operate in regulated markets and, thus, need to prove that their information technology (IT) systems comply with applicable compliance regulations.

IT systems implement fine-grained access control mechanisms to protect assets of the enterprise and to comply with regulations, e.g., the Sarbanes-Oxley Act (SoX) in the financial sector, the Health Insurance Portability and Accounting Act (HIPAA) in the healthcare sector. In general, access control cannot fully capture all requirements. For exceptional situations, for example, it is difficult to formulate access control policies taking all possible legitimate accesses into account. For example, a physician requiring access to a patient's information in an emergency situation, while the physician and patient do not already have a treatment relationship established.

Exceptional access control is an approach for allowing users to override access control decisions, e.g., in emergency situations. Different approaches and techniques have been presented to enable users to override access control restrictions in a controlled manner.

SUMMARY

Implementations of the present disclosure include computer-implemented methods for enforcing dynamic access control constraints of a plurality of access control policies. In some implementations, methods include actions of receiving a set of ordered policies, determining a set of active policies including one or more policies in the set of ordered policies, determining an access control decision based on at least a first policy in the set of active policies, the access control decision being based on determining whether one of a permit decision and a deny decision is inherited from a second policy in the set of ordered policies, and transmitting the access control decision for enforcement of the access control policy.

These and other implementations optionally include on or more of the following features: determining an access control decision includes determining that a permit decision is not inherited, and in response inducing evaluation of the access control request based on the first policy; actions further include determining that the access control request evaluates to a permit decision, and in response, determining whether a deny decision is inherited; in response to determining that a deny decision is inherited, setting the access control decision to deny; the second policy is an inactive policy; policies in the set of ordered policies are ordered from most restrictive to least restrictive; and action further include receiving the access control request from a policy enforcement point.

The present disclosure also provides a computer-readable storage medium coupled to one or more processors and having instructions stored thereon which, when executed by the one or more processors, cause the one or more processors to perform operations in accordance with implementations of the methods provided herein.

The present disclosure further provides a system for implementing the methods provided herein. The system includes one or more processors, and a computer-readable storage medium coupled to the one or more processors having instructions stored thereon which, when executed by the one or more processors, cause the one or more processors to perform operations in accordance with implementations of the methods provided herein.

It is appreciated that methods in accordance with the present disclosure can include any combination of the aspects and features described herein. That is, methods in accordance with the present disclosure are not limited to the combinations of aspects and features specifically described herein, but also include any combination of the aspects and features provided.

The details of one or more implementations of the present disclosure are set forth in the accompanying drawings and the description below. Other features and advantages of the present disclosure will be apparent from the description and drawings, and from the claims.

DESCRIPTION OF DRAWINGS

Like reference symbols in the various drawings indicate like elements.

DETAILED DESCRIPTION

Figure 1:
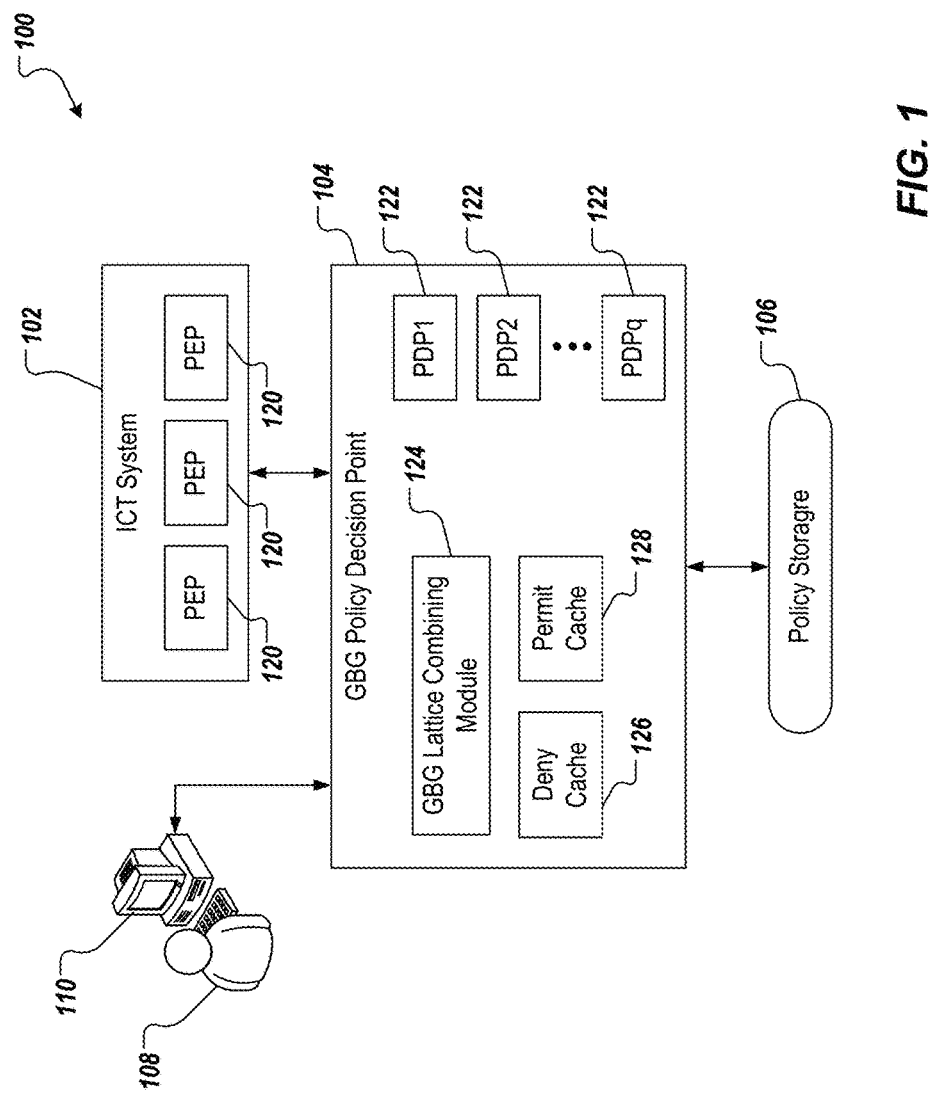
FIG. 1 depicts an example high-level architecture in accordance with implementations of the present disclosure.

Implementations of the present disclosure are generally directed to specifying and enforcing access control constraints that are to be enforced at any time. More particularly, implementations of the present disclosure provide a hierarchical ordering of access control policies that enable fine-grained overriding of negative access control decision, e.g., denies. In some implementations, the hierarchical ordering is provided in a lattice of access control policies. In some examples, the lattice is extended with so called deny policies that explicitly specify DENY decisions that cannot be overridden. As described in further detail herein, implementations of the present disclosure provide fine-grained definition of exceptional system accesses, while ensuring that certain restrictions are enforced under any circumstances. In particular, implementations of the present disclosure provide maintainability and efficient runtime enforcement of policies.

As introduced above, systems need to be more flexible to react to changes during runtime. Systems, such as enterprise systems, for example, implement dynamic access control to adapt due to short-term changes. In some examples, dynamic access control refers to techniques that allow permissions assigned to users to be changed ad-hoc. In this manner, dynamic access control enables the enterprise system to react to planned and unplanned (exceptional) changes in the processes, which require a dynamic change of available permissions.

One technique to achieve such flexibility is referred to as "break-glass," in which users can, if they confirm that an exceptional situation occurred, extend their access rights up to a specific level. For example, in response to an access control decision denying a user's request to access a resource, e.g., application, data, a user interface (UI) can be displayed to the user, and can include a user-selectable element enabling the user to override the access control decision. While allowing users to dynamically override (or ignore) access control restrictions prevents the risk of hindering people to execute tasks, it creates the risk of non-compliance with applicable regulations, e.g., the Sarbanes-Oxley Act (SoX) in the financial sector, the Health Insurance Portability and Accounting Act (HIPAA) in the healthcare sector. Some regulations, for example, require that particular access control restrictions cannot be overridden. That is, the enterprise must guarantee that, at any point in time, no user is able override the particular access control restrictions.

With existing dynamic access control approaches, it is hard to ensure that particular access control constraints that are required by compliance regulations are not violated. Some approaches rely on static checks that have to ensure that granted (exceptional) permissions do not enable users to violate constraints at runtime. This is particularly difficult to address using policy languages, e.g., extensible access control markup language (XACML), that allow complex security policies to be expressed. Some approaches enable a static set of constraints to be defined, which must not be violated. However, because the never-violate rule is static for these constraints, dynamic flexibility is not provided. For example, a situation may occur, in which a constraint has to be intentionally violated, e.g., when some weak constraint has to be violated to relieve a system from a dead lock, when a violation can be compensated with a manual post-hoc action and the compensation is cheaper than the damage caused by not executing the action violating the constraint.

In view of the foregoing, implementations of the present disclosure support the straight-forward specification of constraints and compliance regulations that can be selectively overridden in a controlled manner, e.g., either only at some specified level or not at all. Implementations of the present disclosure are generic and can be adapted to a wide range of existing access control model and policy languages, e.g., XACML. Implementations of the present disclosure can also be used on top of existing solutions and as an extension to products. In this manner, existing products can be enhanced with the flexibility provided by dynamic access control of the present disclosure.

FIG. 1 depicts an example system architecture 100 in accordance with implementations of the present disclosure. The example system architecture 100 includes an example service-oriented architecture (SOA) environment. It is contemplated, however, that implementations of the present disclosure can be applicable in any appropriate type of environment, e.g., cloud-based environments.

In some examples, SOAs provide business services by orchestrating a set of loosely coupled technical services. In some examples, policy-based authentication and authorization in such systems rely on centralized components. In some examples, single sign-on protocols, e.g., using security assertion markup language (SAML), provide a comfortable way to authenticate users within distributed systems using a centralized authentication server storing user credentials, e.g., username, password. Similarly, authorization can be provided by the centrally managed and administered policy decision point (PDP). In some examples, the PDP accesses stored access control policies for all secured services and evaluates access control requests, e.g., requests asking whether a particular user is allowed to access a certain resource (application, data), based on the access control policy. In some examples, enforcement of the access control policy is decentralized, e.g., each and every secured service embeds a policy enforcement point (PEP) that enforces the access control policy based on the response to the access control request from the PDP.

FIG. 1 depicts a generic security architecture for SOA-based systems that use decentralized PEPs to send access control requests to a central PDP for evaluating access control policies. In the example of FIG. 1, the example system architecture 100 includes an information and communication technology (ICT) system 102, a generic break-glass (GBG) PDP 104, and a policy store 106. In some examples, the ICT system 102 and the GBG PDP 104, and the GBG PDP 104 and the policy store 106 can communicate with one another through one or more communication channels. An example communications channel includes a network, e.g., a large computer network, such as a local area network (LAN), a wide area network (WAN), the Internet, a cellular network, or a combination thereof.

The example system architecture 100 further includes a computing device and an administrator. In some examples, the computing device communicates with the GBG PDP 104 using one or more communications channels. In some examples, the administrator 108 can interact with the GBG PDP 104 using the computing device 110.

In some implementations, the ICT system 102 can represent one of a plurality of ICT systems that can interact with the GBG PDP 104. Example ICT systems can include an enterprise resource planning (ERP) system and a customer relationship management (CRM) system. In some implementations, the ICT system 102 submits access control requests to the GBG PDP 104, which provides an access control decision to the ICT system 102 in response. More particularly, the ICT system 102 includes one or more PEPs 120 that can each submit an access control request to the GBG PDP 104. For example, a user using the ICT system 102 can request access to a resource, e.g., an application, data. In response, a respective PEP 120 submits an access control request to the GBG PDP 104, which processes attributes provided for the request in view of one or more access control policies, and provides an access control decision, e.g., PERMIT, DENY. The PEP 120 enforces the access control decision within the ICT system 102, e.g., allows access to the resource in view of a PERMIT decision, blocks access to the resource in view of a DENY decision.

In some implementations, the GBG PDP 104 provides fine-grained overriding of access control decisions, e.g., DENY decisions. More particularly, and in accordance with implementations of the present disclosure, the GBG PDP 104 implements a lattice of access control policies (a policy lattice) that is extended with so called deny policies, which explicitly specify DENY decisions that cannot be overridden. In the example of FIG. 1, the GBG PDP 104 includes a plurality of PDPs 122, a GBG lattice combining module 124, a deny cache 126 and a permit cache 128. In some examples, the GBG PDP 104 is the central PDP for all ICT system 102, e.g., of a given enterprise.

In some implementations, the GBG PDP 104 provides an interface to the administrator 108 for activating and deactivating policies, as well as deploying and updating policies in the policy store 106. In some examples, the GBG lattice combining module 124 implements the lattice combining algorithms in accordance with the present disclosure. In some examples, the GBG lattice combining module 124 evaluates access control requests using one or more of the PDPs 122. In some examples, each PDP 122 is a standard PDP that supports the underlying access control language, e.g., XACML. In some examples, at least one PDP 122 is needed. In some examples, one PDP is needed for each break-glass policy that is to be evaluated. In the case of a single PDP 122, each policy of a plurality of policies would be evaluated sequentially, and the GBG lattice combining module 124 can combine the results. In the case of multiple PDPs 122, policies can be evaluated in parallel and the GBG lattice combining module 124 combines the results accordingly. In some examples, the deny cache 126 stores the denied requests for improving performance, as described in further detail herein. For example, the deny cache 126 can store the access control request, as well as the underlying information associated with the request, e.g., attributes. In some examples, the permit cache 126 stores the permitted requests for improving performance, as described in further detail herein. For example, the permit cache 128 can store the access control request, as well as the underlying information associated with the request, e.g., attributes.

An example high-level workflow in view of the example architecture 100 of FIG. 1 will now be described. A user requests access to a resource, e.g., a patient record, of the ICT system 102. A respective PEP 120 generates an access control request, and sends the access control request, and, in some cases, information required for evaluating the access control request to the GBG PDP 104. The GBG PDP 104 implements the lattice combining algorithm, as described herein, based on the set of active access control policies, to evaluate the access control request. In some examples, the GBG lattice combining module 124 uses the deny cache 126 and/or the permit cache 128 for the evaluation. In some examples, the GBG lattice combining module 124 forwards the access control request to the corresponding PDP(s) 122. For example, if the GBG lattice combining module 124 cannot evaluate the request based on information provided in the deny cache 126 and/or the permit cache 128, the request can be forwarded to one or more of the PDPs 122 for respective evaluations. In some examples, GBG lattice combining module 124 receives results from one or more of the PDPs 122, and combines the results to provide the access control decision. In some examples, the result is stored in the deny cache 126 and/or the permit cache 128. The GBG PDP 104 returns the access control decision to the respective PEP 120

As introduced above, implementations of the present disclosure are directed to specifying and enforcing access control constraints that are enforced at any time. Example access control constraints include negative permissions, such as denying access of a user to a resource, e.g., not giving permission to the user to access the resource. As described in further detail herein, implementations of the present disclosure provide a hierarchical ordering of polices (a policy lattice) that enables overrides of policies to be controlled in a fine-grained manner, and provide an explicit specification, e.g., for each level/policy, that cannot be overridden. As also described in further detail herein, implementations of the present disclosure are supported by an effective and efficient runtime enforcement framework that supports various infrastructures (e.g., service-oriented infrastructures, cloud-based infrastructures).

In some implementations, and as described in further detail below, flexible access control can be provided by selectively activating (or deactivating) one or more policies in the policy lattice. For example, for a particular time period, a policy can be active, e.g., access control requests are evaluated against the policy, and for another time period, the policy can be inactive, e.g., access control requests are not evaluated against the policy. In some examples, and as described in further detail herein, a policy in the policy lattice inherits an access control decision, e.g., a PERMIT decision, a DENY decision, from one or more other policies in the policy lattice. In some examples, an administrator, e.g., the administrator 108 of FIG. 1, can activate/deactivate one or more policies. In some examples, activation/deactivation can be automatically performed, e.g., on a schedule defined by an administrator.

Figure 2:
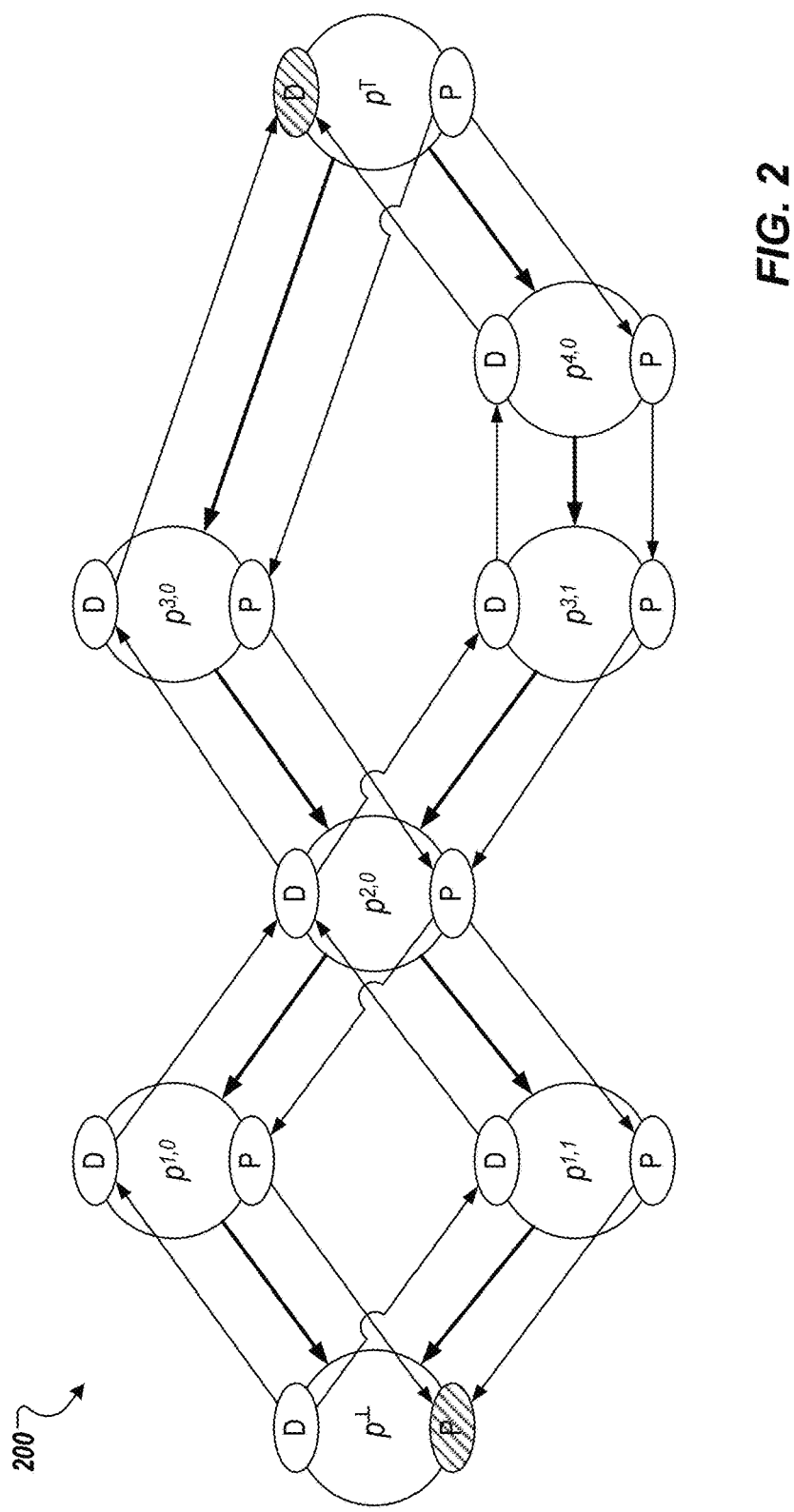
FIG. 2 depicts a block diagram of a conceptual architecture in accordance with implementations of the present disclosure.

Implementations of the present disclosure provide a user-friendly specification, referred to herein as generic (and flexible) break-glass (GBG) for specifying and enforcing access control constraints that must be enforced at any time. In accordance with GBG, every policy p has two parts, and one or both can be empty. Example parts include permit policies $p_P$ and deny policies $p_D$. In some examples, permit policies define permissions that should be granted to users. In some examples, deny policies define constraints, e.g., which actions would violate legal constraints and are not permitted. In some implementations, the policies are ordered in lattice that defines a refinement structure. In some examples, the policy lattice is ordered based on how restrictive respective policies are. For example, the (conceptually) most restrictive policy $p^\perp$ denies everything, and is extended with policies permitting more and more toward the (conceptually) most permitting policy pT, which permits everything. FIG. 2 depicts an example policy lattice 200 in accordance with implementations of the present disclosure.

Following the refinement structure, permissions are inherited from the policy $p^\perp$ toward the policy pT, permitting more and more. For example, compared to the policy $p^{2,0}$, the permit-parts of the policies $p^\perp$, $p^{1,0}$, and $p^{1,1}$ are less permissive and the permit-parts of the policies $p^{3,0}$, $p^{3,1}$, $p^{4,0}$, and pT are more permissive. For the deny-parts, $p^\perp$, $p^{1,0}$, and $p^{1,1}$ are more restrictive than the deny-part of $p^{2,0}$, and the deny-parts of $p^{3,0}$, $p^{3,1}$, $p^{4,0}$ are less restrictive. Consequently, access requests that are denied due to a constraint violation in $p^{3,1}$ are also denied in all other policies $p^{1,0}$, $p^{1,1}$, and $p^{2,0}$.

In accordance with implementations of the present disclosure, a policy (and, thus, permissions granted thereby) can be activated or deactivated. In this manner, permissions can be activated ad-hoc by an authorized entity, e.g., the administrator 108 of FIG. 1. In some implementations, constraints are always "active" regardless of whether the permissions in the respective policy are activated, because constraints can be overridden only by means of a higher policy. Consequently, the activation of policies only increases permissions, but does not deactivate constraints. For example, if a request is permitted by the permit policy P of the policy $p^{1,1}$, but violates a constraint in the deny policy D of the policy $p^{2,0}$, the request is only granted if at least one of $p^{3,0}$ or $p^{3,1}$ is active.

Implementations of the present disclosure provide a lattice combining algorithm to evaluate policies. In some examples, the lattice combining algorithm does not require any specific format, policy language, or access control model for defining permit and deny policies. Instead, and in accordance with implementations of the present disclosure, ordered policies are processed to guarantee policy properties and to delegate evaluation of permit and deny policies to an engine. In some examples, the engine is capable of the language and format used to define the policies. In some examples, the engine can be internal to a process. In some examples, the engine is provided as an external engine (e.g., running on another machine). In some implementations, focus is spent on found permit decisions from permit policies and found deny decisions from deny policies. In some examples, it is assumed that only permit and deny decisions can be returned by policies. However, it is contemplated that implementations of the present disclosure can be enhanced to include other return values that can be defined by existing access control models or policy languages. For example, in XACML, example return values can include "not applicable" (indicating that no decision can be made), which can be interpreted as deny for permit policies or as permit for deny policies, and "intermediate" (indicating an error in the evaluation), which can be interpreted as deny for permit policies (allowing the algorithm to find some exceptional permission in case of an error and allow for exception handling in the policy itself) or as deny for deny policies.

In some implementations, policies can be identified based in a respective, unique identifier (id). In some implementations, the following example functions are provided: getPoliciesOrdered ( ), getExtPolicies (id), getRefPolicies (id), isActive (id), evaluateP (id) and evaluateD (id). In some examples, getPoliciesOrdered ( ) returns a list of all policy IDs provided in ordered policies (e.g., policies order along a lattice, such as the example lattice 200 of FIG. 2). In some examples, getExtPolicies (id) returns a list of all policy IDs, which extend the policy referenced with id, and getRefPolicies (id) returns a list of all policy IDs, which refine the policy referenced with id. In some examples, isActive (id) returns a value indicating whether the policy is active. In some examples, evaluateP (id) and evaluateD (id) respectively evaluate the permit and deny part of the policy referenced with id, e.g., calling an external engine (a PDP 122 of FIG. 1).

The example listing below provides an example lattice combining algorithm:

Listing 1: Example Lattice Combining Algorithm

```
Map<PolicyId, Result> denyCache; // store (all) DENY results
and)
Map<PolicyId, Result> permitCache; // found PERMITs into a
cache)
Decision combiningAlg( ) {
  for ( policyId id : getPoliciesOrdered( ) ) {
    if ( isActive(id) ) {
      boolean permitted = false;
      if ( isPermitInh(id) ) {
        permitted = true;
      } else {
        Result res = evaluateP(id);
        if ( res == PERMIT ) {
          permitCache.put(id, res);
          permitted = true;
        }
      }
      if ( permitted && ! isDenyInh(id) )
        return ( permitCache.get(id) + getOblg(id) );
    }
  }
  return DENY;
}
boolean isDenyInh (PolicyId id) {
  for ( PolicyId extId : getExtPolicies(id) ) {
    Result res;
    if ( denyCache.contains(extId) ) {
      res = denyCache.get(id);
    } else {
      res = evaluateD(id );
      denyCache.put(id, res);
    }
    if (res == DENY)
      return true;
  }
  return false ;
}
```

Listing 1: Example Lattice Combining Algorithm -continued

```
boolean isPermitInh(PolicyId id) {
  for ( PolicyId refId : getRefPolicies(id) ) {
    if ( permitCache.contains(refId) )
      return true;
  }
  return false ;
}
```

The example lattice combining algorithm of Listing 1 makes use of caches for found decisions, e.g., the deny cache 126 and/or the permit cache 128 of FIG. 1, to avoid the redundant evaluation of policies. In some examples, while the deny cache contains the result of every evaluated deny policy, i.e., permit and deny results, the permit cache only needs to store found permit results, as other results are not relevant for further evaluation. In some examples, the example algorithm iterates over all policies, which are ordered according to a policy lattice that is returned by getPoliciesOrdered ( ). For each policy in the policy lattice, it is determined whether the policy is active. For example, the permit part of a policy can only contribute to the access control decision, if the policy is active. For each active policy, isPermitInh (id) is executed to check whether an inherited permit decision, e.g., from an active extending policy, is already stored in the cache, e.g., the permit cache 128. If no inherited permit is found, the permit part of the current policy (the active policy that is being reviewed) is evaluated, e.g., by a PDP 122 of FIG. 1. If the evaluation of the policy results in a permit decision, the result is stored in the permit cache, e.g., permitCache.put (id, res).

If, for the current policy, a permit is provided, e.g., from the cache or the evaluation result is permit, isDenyInh (id) is performed to determine whether there is an inherited deny from an extending policy for one or more extending policies associated with the current policy. In some examples, a loop iterates over all extending policies using getExtPolicies (id) to retrieve all policies which extend the current policy. In some examples, a list of one or more extending policies can be associated with each policy. In some examples, and with reference to FIG. 2, deny decisions are inherited towards $p^\perp$. Consequently, a search for an inherited deny is performed towards the bottom of the lattice, i.e., along the extending policies.

In some examples, for each extending policy, it is determined whether an inherited deny is stored in the cache, e.g., the deny cache 126 of FIG. 1. In some examples, there is no check as to whether the extending policies are active, because, for example, denies are inherited regardless whether the corresponding extending policy is active. If an inherited deny is not stored in the cache, the deny part of the current extending policy (the extending policy that is being reviewed) is evaluated, e.g., by a PDP 122 of FIG. 1. If the evaluation of the extending policy results in a deny decision, the result is stored in the deny cache, e.g., denyCache.put (id, res), and a DENY decision is returned, e.g., to the PEP. If no deny is found, obligations of the current policy are retrieved. In some examples, obligations are a set of requirements and/or actions that need to be fulfilled to override a DENY. Example obligations can include switching to a system mode, in which all users actions are logged, requiring a manual consent from the user for the override, e.g., by displaying a dialog box which the user has to confirm the override, and informing responsible persons, e.g., a chief information officer, about the override.

In some implementations, the algorithm iterates over all policies in the order defined by the lattice, e.g., returned by getPoliciesOrdered( ). In some examples, if none of the policies results in a deny, the permit(s) are returned along with any obligations.

Figure 3:
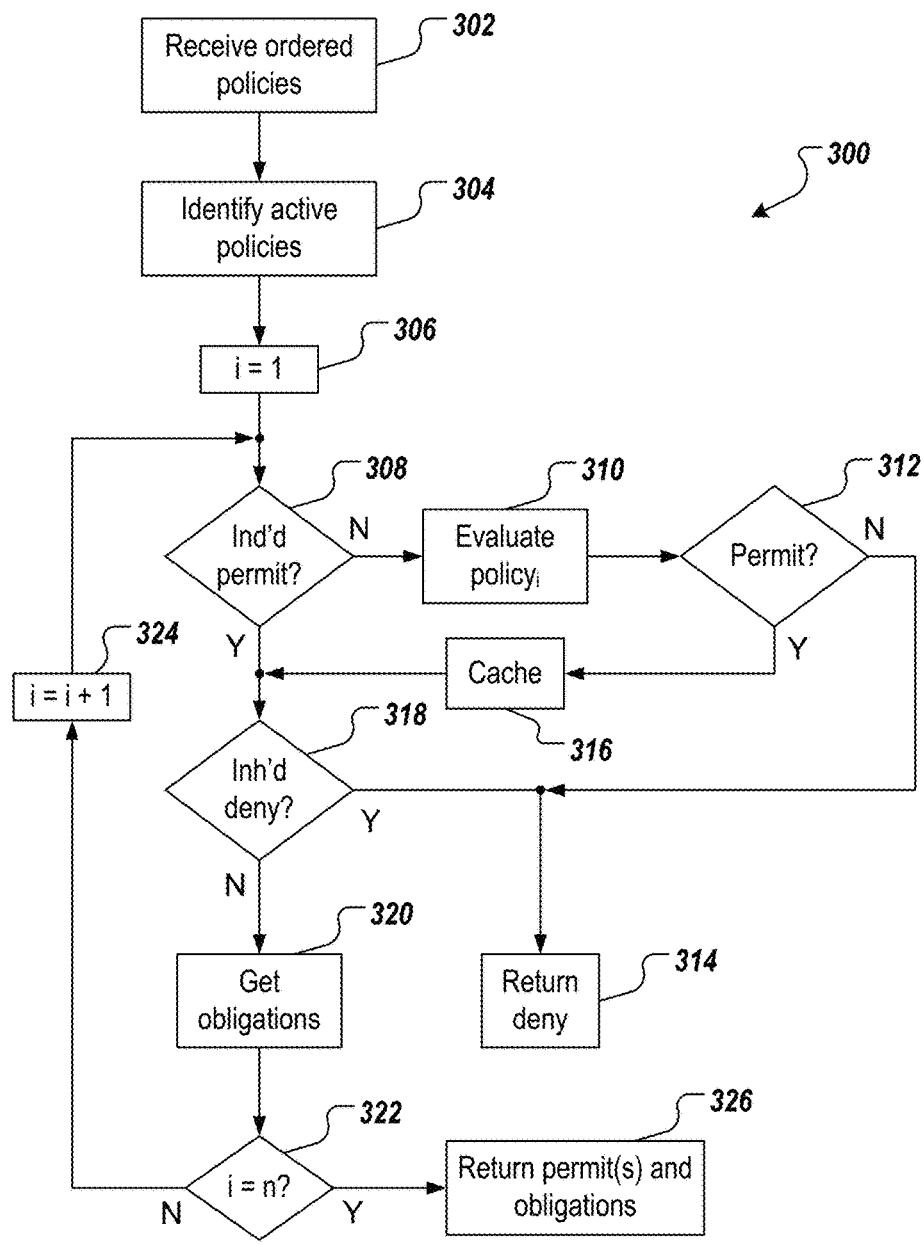
FIG. 3 depicts an example process that can be executed in accordance with implementations of the present disclosure.

FIG. 3 depicts an example process 300 that can be executed in accordance with implementations of the present disclosure. In some examples, the example process 300 can be provided as one or more computer-executable programs executed using one or more computing devices.

Ordered policies are received (302). For example, in response to an access control request received by the GBG PDP 104, a policy lattice is retrieved, e.g., from computer-readable memory, which includes ordered policies. In some examples, the policy lattice is defined by an administrator, e.g., the administrator 108 of FIG. 1, and includes m policies, where m≥2. In some examples, active policies are identified (304). For example, the policy lattice can include n active policies, where n≥1.

A counter i is set equal to 1 (306). For an active policy i, it is determined whether there is an inherited permit (308). For example, and as described above, isPermitInh (id) is executed, where id is the identifier assigned to active policy i, to check whether an inherited permit decision, e.g., from an active extending policy, is already stored in the cache, e.g., the permit cache 128. If an inherited policy is not available, the active policy i is evaluated (310). For example, the access control request (and any required information) is provided to a PDP, e.g., a PDP 122 of FIG. 1, for evaluation, and an access control decision is returned. It is determined whether a permit decision results from the evaluation (312). In some examples, if there is no permit decision, i.e., the evaluation results in a deny decision, a DENY decision is returned (314), and the example process ends. For example, a DENY decision can be returned from the GBG PDP 104 to the corresponding PEP 120, i.e., the PEP 120 that submitted the access control request. If there is a permit decision, the permit decision is stored in the cache (316).

If a permit is inherited (308) or the active policy i evaluates to permit (310, 312), it is determined whether a deny is inherited (318). In some examples, and as described above, it is determined whether a deny is inherited from any policies extending the policy i, regardless of whether the extending policy is active. If a deny is inherited, a DENY decision is returned (314). If a deny is not inherited, any obligations for the active policy i are retrieved (320).

It is determined whether the counter i is equal to n. If i is not equal to n, the counter i is incremented (324), and analysis of the next active policy i is performed. If i is equal to n, all active policies have been evaluated and one or more permits are returned with respective obligations (326). For example, a PERMIT decision can be returned from the GBG PDP 104 to the corresponding PEP 120, i.e., the PEP 120 that submitted the access control request.

The example process 300 depicts sequential analysis of active access control policies, e.g., iteration using the counter i, where the counter i is incremented until all n active policies have been evaluated (assuming no intermediate DENY decision). It is contemplated, however, that the n active policies can be evaluated in parallel, e.g., using a plurality of PDPs 122 of FIG. 1, if needed.

Figure 4:
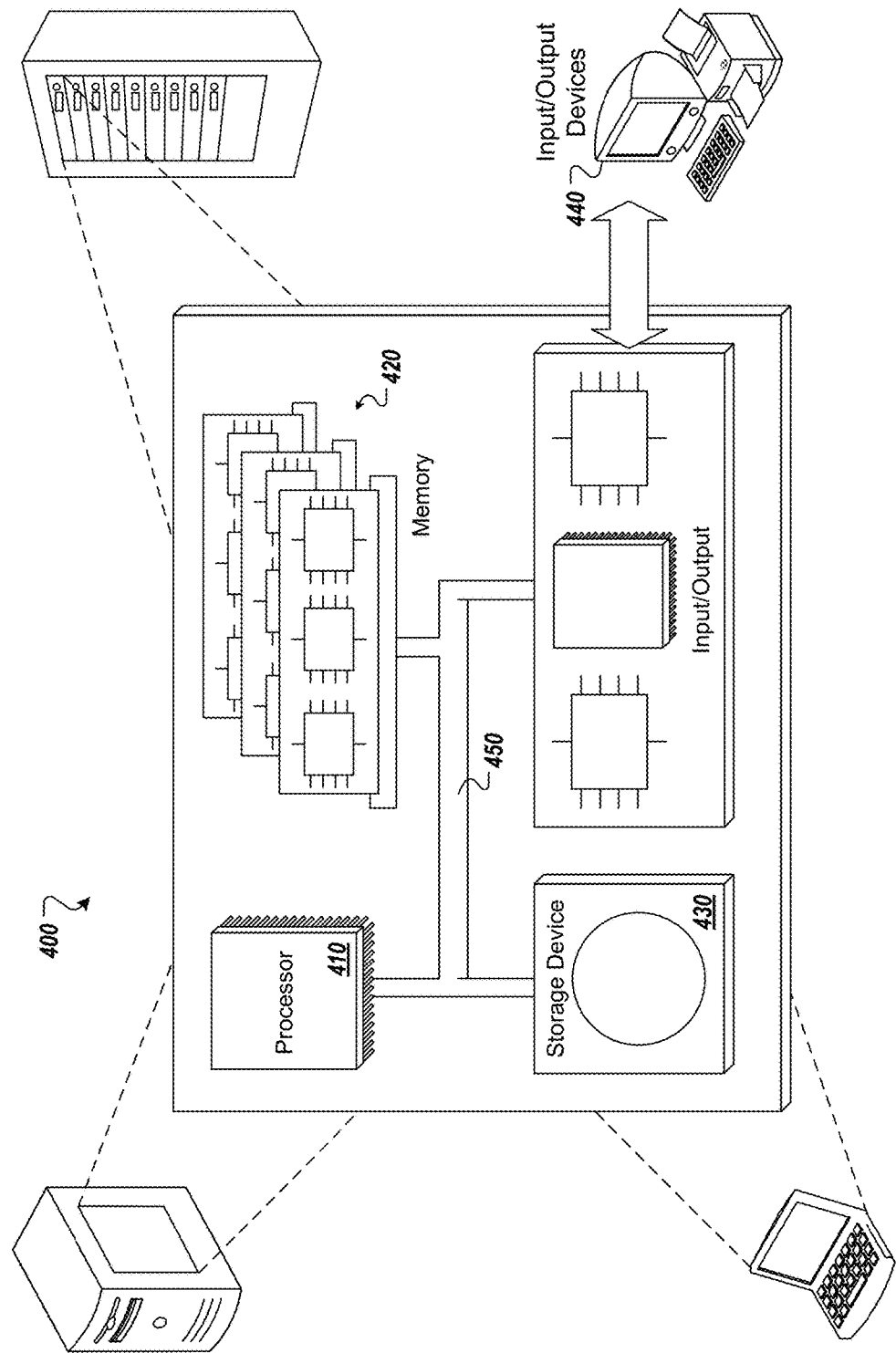
FIG. 4 is a schematic illustration of example computer systems that can be used to execute implementations of the present disclosure.

Referring now to FIG. 4, a schematic diagram of an example computing system 400 is provided. The system 400 can be used for the operations described in association with the implementations described herein. For example, the system 400 may be included in any or all of the server components discussed herein. The system 400 includes a processor 410, a memory 420, a storage device 430, and an input/output device 440. The components 410, 420, 430, 440 are interconnected using a system bus 450. The processor 410 is capable of processing instructions for execution within the system 400. In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the system 400. In one implementation, the memory 420 is a computer-readable medium. In one implementation, the memory 420 is a volatile memory unit. In another implementation, the memory 420 is a non-volatile memory unit. The storage device 430 is capable of providing mass storage for the system 400. In one implementation, the storage device 430 is a computer-readable medium. In various different implementations, the storage device 430 may be a floppy disk device, a hard disk device, an optical disk device, or a tape device. The input/output device 440 provides input/output operations for the system 400. In one implementation, the input/output device 440 includes a keyboard and/or pointing device. In another implementation, the input/output device 440 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. Elements of a computer can include a processor for executing instructions and one or more memories for storing instructions and data. Generally, a computer can also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

A number of implementations of the present disclosure have been described. Nevertheless, it will be understood that various modifications may be made without departing from the spirit and scope of the present disclosure. Accordingly, other implementations are within the scope of the following claims.

What is claimed is:

1. A computer-implemented method for enforcing dynamic access control constraints of a plurality of access control policies, the method being executed using one or more processors and comprising:
   receiving, by the one or more processors, a set of ordered policies that are ordered according to a policy lattice defining a hierarchy from most restrictive policies to least restrictive policies, the policy lattice combining an access control algorithm, a deny cache storing previously denied requests, and a permit cache storing previous access control requests, the policy lattice enabling access control overriding for a first portion of policies that are controlled in a fine-grained manner and providing an explicit access control specification for a second portion of policies that are enforceable at any time;
   determining, by the one or more processors, a set of active policies comprising one or more policies in the set of ordered policies, the set of active policies being used in evaluating an access control request during a particular time period;
   determining, by the one or more processors, an access control decision based on at least a first policy in the set of active policies, the access control decision being based on operations comprising:
      determining whether one of a permit decision and a deny decision is inherited from a second policy in the set of ordered policies that extends from the first policy in the set of active policies based on the policy lattice, the permit decision being inherited if the second policy is active and the deny decision being inherited regardless whether the second policy is active, and
      in response to determining that the permit decision and the deny decision are not inherited from the second policy, evaluating the first policy in the set of active policies based on the policy lattice; and
   transmitting, by the one or more processors, the access control decision for enforcement of the access control policy.

2. The method of claim 1, wherein determining an access control decision comprises determining that a permit decision is not inherited, and in response inducing evaluation of an access control request based on the first policy.

3. The method of claim 2, further comprising determining that the access control request evaluates a permit decision, and in response, determining whether a deny decision is inherited.

4. The method of claim 3, wherein, in response to determining that a deny decision is inherited, setting the access control decision to deny.

5. The method of claim 1, wherein the second policy is an inactive policy.

6. The method of claim 1, wherein the most restrictive policies define impermissible actions that would violate legal constraints and the least restrictive policies define permissions grantable to users with associated obligations.

7. The method of claim 1, further comprising receiving an access control request from a policy enforcement point.

8. A non-transitory computer-readable storage medium coupled to one or more processors and having instructions stored thereon which, when executed by the one or more processors, cause the one or more processors to perform operations for enforcing dynamic access control constraints of a plurality of access control policies, the operations comprising:
   receiving a set of ordered policies that are ordered according to a policy lattice defining a hierarchy from most restrictive policies to least restrictive policies, the policy lattice combining an access control algorithm, a deny cache storing previously denied requests, and a permit cache storing previous access control requests, the policy lattice enabling access control overriding for a first portion of policies that are controlled in a fine-grained manner and providing an explicit access control specification for a second portion of policies that are enforceable at any time;
   determining a set of active policies comprising one or more policies in the set of ordered policies, the set of active policies being used in evaluating an access control request during a particular time period;
   determining an access control decision based on at least a first policy in the set of active policies, the access control decision being based on operations comprising:
      determining whether one of a permit decision and a deny decision is inherited from a second policy in the set of ordered policies that extends from the first policy in the set of active policies based on the policy lattice, the permit decision being inherited if the second policy is active and the deny decision being inherited regardless whether the second policy is active, and in response to determining that the permit decision and the deny decision are not inherited from the second policy, evaluating the first policy in the set of active policies based on the policy lattice; and transmitting the access control decision for enforcement of the access control policy.

9. The computer-readable storage medium of claim 8, wherein determining an access control decision comprises determining that a permit decision is not inherited, and in response inducing evaluation of an access control request based on the first policy.

10. The computer-readable storage medium of claim 9, wherein operations further comprise determining that the access control request evaluates to a permit decision, and in response, determining whether a deny decision is inherited.

11. The computer-readable storage medium of claim 10, wherein, in response to determining that a deny decision is inherited, setting the access control decision to deny.

12. The computer-readable storage medium of claim 8, wherein the second policy is an inactive policy.

13. The computer-readable storage medium of claim 8, wherein policies in the set of ordered policies are ordered from most restrictive to least restrictive.

14. The computer-readable storage medium of claim 8, wherein operations further comprise receiving an access control request from a policy enforcement point.

15. A system, comprising:
a computing device; and
a computer-readable storage device coupled to the computing device and having instructions stored thereon which, when executed by the computing device, cause the computing device to perform operations for determining weights for enforcing dynamic access control constraints of a plurality of access control policies, the operations comprising:
receiving a set of ordered policies that are ordered according to a policy lattice defining a hierarchy from most restrictive policies to least restrictive policies, the policy lattice combining an access control algorithm, a deny cache storing previously denied requests, and a permit cache storing previous access control requests, the policy lattice enabling access control overriding for a first portion of policies that are controlled in a fine-grained manner and providing an explicit access control specification for a second portion of policies that are enforceable at any time;

determining a set of active policies comprising one or more policies in the set of ordered policies, the set of active policies being used in evaluating an access control request during a particular time period;

determining an access control decision based on at least a first policy in the set of active policies, the access control decision being based on operations comprising:

determining whether one of a permit decision and a deny decision is inherited from a second policy in the set of ordered policies that extends from the first policy in the set of active policies based on the policy lattice, the permit decision being inherited if the second policy is active and the deny decision being inherited regardless whether the second policy is active, and in response to determining that the permit decision and the deny decision are not inherited from the second policy, evaluating the first policy in the set of active policies based on the policy lattice; and transmitting the access control decision for enforcement of the access control policy.

16. The system of claim 15, wherein determining an access control decision comprises determining that a permit decision is not inherited, and in response inducing evaluation of an access control request based on the first policy.

17. The system of claim 16, wherein operations further comprise determining that the access control request evaluates to a permit decision, and in response, determining whether a deny decision is inherited.

18. The system of claim 17, wherein, in response to determining that a deny decision is inherited, setting the access control decision to deny.

19. The system of claim 15, wherein the second policy is an inactive policy.

20. The system of claim 15, wherein policies in the set of ordered policies are ordered from most restrictive to least restrictive.

* * * * *